US006900300B1

(12) United States Patent
Erikson et al.

(10) Patent No.: US 6,900,300 B1
(45) Date of Patent: *May 31, 2005

(54) QUADRUPLEX DNA AND DUPLEX PROBE SYSTEMS

(75) Inventors: Glen H. Erikson, Providentiales (TC); Jasmine I. Daksis, Richmond Hill (CA)

(73) Assignee: Ingeneus Corporation, Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 09/664,827

(22) Filed: Sep. 19, 2000

(51) Int. Cl.[7] .......................... C07H 21/02; C07H 21/04; C12Q 1/68
(52) U.S. Cl. .......................... 536/23.1; 536/24.33; 435/6
(58) Field of Search .......................... 536/23.1, 24.32, 536/24.31, 24.3, 24.33, 24.5, 25.4; 435/6; 200/274

(56) References Cited

U.S. PATENT DOCUMENTS

| | | | | |
|---|---|---|---|---|
| 5,451,502 A | * | 9/1995 | George, Jr. ................... | 435/6 |
| 5,451,503 A | * | 9/1995 | Hogan et al. ................. | 435/6 |
| 5,874,555 A | | 2/1999 | Dervan et al. ............. | 536/231 |
| 5,888,739 A | | 3/1999 | Pitner et al. .................. | 435/6 |
| 5,912,332 A | | 6/1999 | Agrawal et al. ........... | 536/23.1 |
| 5,948,897 A | * | 9/1999 | Sen et al. .................. | 536/22.1 |
| 6,017,709 A | | 1/2000 | Hardin et al. ................. | 435/6 |
| 6,255,469 B1 | | 7/2001 | Seeman et al. | |
| 6,287,772 B1 | | 9/2001 | Stefano et al. | |
| 6,312,925 B1 | | 11/2001 | Meyer, Jr. et al. | |
| 6,420,115 B1 | * | 7/2002 | Erikson et al. ............... | 435/6 |

FOREIGN PATENT DOCUMENTS

| | | |
|---|---|---|
| GB | 2333359 A | 7/1999 |
| GB | 2338301 A | 12/1999 |
| WO | WO 97/45539 A | 12/1997 |
| WO | WO 97/45539 A1 | 12/1997 |
| WO | WO 00/20633 A1 | 4/2000 |
| WO | WO 00 43543 A | 7/2000 |

OTHER PUBLICATIONS

McGavin et al. A computer graphics study of multistranded DNA models. J. Mol. Graphics., vol. 7, pp. 218–232, 1989.*
McGavin et al. A computer graphics study of multistranded DNA models. J. Mol. Graphics., vol. 7, pp. 218–232, 1989.*
McGavin et al. A computer graphics study of multistranded DNA models. J. Mol. Graphics., vol. 7, pp. 218–232, 1989.*
Sinden R. DNA structure and function. Academic Press, Inc., pp. 225–227, 1994.*
Sinden R. DNA structure and function. Academic Press, Inc., pp. 225–227, 1994.*
McGavin, "Models of Specifically Paired Like (Homologous) Nucleic Acid Structures," *J. Mol. Biol.* (1971) 55, 293–298.
McGavin, "Relationships and Transformations Between Some Nucleic Acid Models," *J. Theor. Biol.* (1980) 85, 665–672.
McGavin, "Four Strand Recombination Models," *J. Theor. Biol.* (1989) 136, 135–150.
McGavin, "Four–Strand Structure, Kinks and Cruciforms in DNA," *J. Theor. Biol.* (1989) 138, 117–128.
McGavin et al., "A Computer Graphics Study of Multistranded DNA Models," J. Mol Graphics. (1989) 7, 218–232.
Lishanski et al., "Branch migration inhibition in PCR–amplified DNA; homogeneous mutation detection", *Nucleic Acids Research*, vol. 28, No. 9, pp. e42i–e42 vii, (May 1, 2000).
Deng et al., "Duplex to quadruplex equilibrium of the self–complementary oligonucleotide" *Biopolymer*, vol. 35, No. 6, pp. 677–681, (1995).
Salisbury et al., The bi–loop, a new general four–stranded DNA motif, *Prol. Natl. Acad. Sci. USA.* vol. 94, pp. 5515–5518 (May 1997).
Eckhart, et al., *The Journal of Biological Chemistry*, vol. 274, No. 5, pp. 2613–2615, (Jan. 29, 1999).
Rocher, Christophe et al., *Nucleic Acids Research*, "Initiation of DNA replication by DNA polymerases from primers forming a triple helix," 2001, vol. 29, No. 16, 3320–3326.
Sen et al., Nature 334:364–366 (1988).
Williamson et al. Cell 59:871–880 (1989).
Sen et al., Biochemistry 31:65–70 (1992).
Marsh et al., Biochemistry 33:10718–10724 (1994).
Marsh et al., Nucl. Acids Res. 23:696–700 (1995).
Mazumder et al., Biochemistry 35:13762–13771 (1996).
Carlsson et al., Nature 380:207 (1996).
Baran et al., Nucleic Acids Research 25:297–303 (1997).
Floris, et al., "Effect of cations on purine–purine–pyrimidine", 260 Eur. J. Biochem. 801–809 (1999).
U.S. Appl. No. 09/224,505, Daksis et al.
U.S. Appl. No. 09/468,679, Daksis et al.
U.S. Appl. No. 09/613,263, Erikson et al.

* cited by examiner

*Primary Examiner*—Jeffrey Fredman
*Assistant Examiner*—Suryaprabha Chunduru
(74) *Attorney, Agent, or Firm*—Caesar, Rivise, Bernstein, Cohen & Pokotilow, Ltd.

(57) ABSTRACT

A multiplex structure, such as a nucleic acid quadruplex, includes: a first strand containing a first sequence of nucleobases; a second strand containing a second sequence of nucleobases, wherein the second strand is associated with the first strand by Watson-Crick bonding; a third strand containing a third sequence of nucleobases; and a fourth strand containing a fourth sequence of nucleobases, wherein the fourth strand is associated with the second strand and the third strand by Watson-Crick bonding. Formation of the multiplex structure is promoted by monovalent cations (e.g., sodium and potassium), divalent cations, multivalent cations, intercalating agents and/or molecules known to bind within the minor grooves of nucleic acids. The multiplex structure and the process of forming it have diagnostic, therapeutic, prophylactic and nanoengineering applications.

45 Claims, 6 Drawing Sheets

FIG. 1. Mix of 15-mer dsDNA-F (4 pmole) (53% GC) and 50-mer dsDNA (0.4 pmole) in the presence of 100 mM KCl (after 1 hr)

FIG. 2. Mix of 15-mer dsDNA-F (4 pmole) (53% GC) and 50-mer dsDNA (0.4 pmole) in the presence of divalent cations (after 1 hr)

FIG. 4. Mix of 15-mer dsDNA (4 pmole) (53% GC) and 50-mer dsDNA (0.4 pmole) in the presence of 100 nM YOYO-1

FIG. 5. Mix of 15-mer dsDNA (4 pmole) (53% GC) and 50-mer ssDNA (0.4 pmole) in the presence of 100 nM YOYO-1

Fig. 6

QUADRUPLEX DNA AND DUPLEX PROBE SYSTEMS

BACKGROUND OF THE INVENTION

1. Field of Invention

The invention relates to nucleic acid multiplexes, and more particularly to methods wherein quadruplexes are formed by specific binding between double-stranded nucleic acid probes and double-stranded nucleic acid target sequences.

2. Description of Related Art

Although nucleic acid duplexes are the most widely studied type of multiple-strand nucleic acid structures, it has been discovered that nucleic acids also form triplex and quadruplex structures under certain conditions.

Until recently, hybridization among three nucleic acid strands to form a triplex was widely believed to be confined to very limited species of nucleic acids (e.g., polypurine or polypyrimidine sequences). See, e.g., Floris et al., "Effect of cations on purine-purine-pyrimidine triple helix formation in mixed-valence salt solutions," 260 Eur. J. Biochem. 801–809 (1999). Moreover, triplex formation or hybridization was thought to be based on Hoogsteen binding between limited varieties of adjacent nucleobases, rather than Watson-Crick base pairing. See, e.g., Floris et al. and U.S. Pat. No. 5,874,555 to Dervan et al. However, the inventors have recently disclosed in several patent applications that triplex nucleic acids based on Watson-Crick base pairing can be created and used as the basis for a highly accurate and sensitive assay for specific binding. See U.S. patent application Ser. Nos. 09/613,263 and 09/468,679, respectively filed Jul. 10, 2000 and Dec. 21, 1999.

As was the case with triplex nucleic acids, the conventional wisdom regarding quadruplex nucleic acids has been that such peculiar structures only exist under relatively extreme conditions for a relatively narrow class of nucleic acids. In particular, Sen et al. (Nature 334:364–366 (1988)) disclosed that guanine-rich oligonucleotides can spontaneously self-assemble into four-stranded helices in vitro. Sen et al. (Biochemistry 31:65–70 (1992)) disclosed that these four-stranded complexes can further associate into superstructures composed of 8, 12, or 16 oligomers.

Marsh et al. (Biochemistry 33:10718–10724 (1994), and Nucleic Acids Research 23:696–700 (1995)) disclosed that some guanine-rich oligonucleotides can also assemble in an offset, parallel alignment, forming long "G-wires". These higher-order structures are stabilized by G-quartets that consist of four guanosine residues arranged in a plane and held together through Hoogsteen base pairings. According to Sen et al. (Biochemistry 31:65–70 (1992)), at least three contiguous guanines within the oligomer are critical for the formation of these higher order structures.

It has been suggested that four-stranded DNAs play a role in a variety of biological processes, such as inhibition of HIV-1 integrase (Mazumder et al., Biochemistry 35:13762–13771 (1996)), formation of synapsis during meiosis (Sen et al., Nature 334:364–366 (1988)), and telomere maintenance (Williamson et al., Cell 59:871–880 (1989)); Baran et al., Nucleic Acids Research 25:297–303 (1997)).

It has been further suggested that controlling the production of guanine-rich quadruplexes might be the key to controlling such biological processes. For example, U.S. Pat. No. 6,017,709 to Hardin et al. suggests that telomerase activity might be controlled through drugs that inhibit the formation of guanine quartets.

U.S. Pat. No. 5,888,739 to Pitner et al. discloses the G-quartet based quadruplexes can be employed in an assay for detecting nucleic acids. Upon hybridization to a complementary oligonucleotide, the G-quartet structure unfolds or linearizes, thereby increasing the distance between a donor and an acceptor on different parts of the G-quartet structure, resulting in a decrease in their interaction and a detectable change in a signal (e.g., fluorescence) emitted from the structure.

U.S. Pat. No. 5,912,332 to Agrawal et al. discloses a method for the purification of synthetic oligonucleotides, wherein the synthetic oligonucleotides hybridize specifically with a desired, full-length oligonucleotide and concomitantly form a multimer aggregate, such as quadruplex DNA. The multimer aggregate containing the oligonucleotide to be purified is then isolated using size-exclusion techniques.

Despite the foregoing developments, the full potential of quadruplex nucleic acid has neither been fully appreciated nor fully exploited.

All references cited herein are incorporated herein by reference in their entireties.

SUMMARY OF THE INVENTION

The invention provides a multiplex structure comprising: a first strand containing a first sequence of nucleobases; a second strand containing a second sequence of nucleobases, wherein the second strand is associated with the first strand by Watson-Crick bonding; a third strand containing a third sequence of nucleobases; and a fourth strand containing a fourth sequence of nucleobases, wherein the fourth strand is associated with the second strand and the third strand by Watson-Crick bonding.

Also provided is a method for providing the multiplex structure of the invention. The method comprises: providing a hybridization medium comprising the first strand, the second strand, the third strand, the fourth strand, water, a buffer and at least one promoter; and incubating the hybridization medium for an incubation time effective to hybridize the second strand to the fourth strand to provide the multiplex structure.

Still further provided is an assay for single-stranded and double-stranded targets employing a double-stranded probe.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Unlike the quadruplexes discussed in the Background Section above, the preferred multiplex structures of the invention contain at least four strands of nucleic acid bonded together according to traditional Watson-Crick bonding rules.

As used herein, the term "Watson-Crick bonding" is intended to define specific association between opposing pairs of nucleic acid (and/or nucleic acid analogue) strands via matched, opposing bases. While the formation of a Watson-Crick quadruplex may sometimes be referred to as a hybridization event herein, that is merely for convenience and is not intended to limit the scope of the invention with respect to how the formation of a Watson-Crick quadruplex can be best characterized.

The multiplex structures of the invention are preferably quadruplexes. Each strand of the multiplex independently comprises a nucleic acid or a nucleic acid analogue. Suitable nucleic acids include, e.g., DNA or RNA. Preferred nucleic acid analogues contain an uncharged or partially charged backbone (i.e., a backbone having a charge that is not as negative as a native DNA backbone).

In certain embodiments, one of the second and fourth strands of the four-stranded quadruplex comprises DNA and the other of the second and fourth strands comprises RNA, mRNA, hnRNA, rRNA, tRNA or cDNA.

In certain embodiments, the second strand and the fourth strand are anti-parallel to each other. These embodiments are defined as having mirror complementarity. In these embodiments, a major groove of the first and second strands is placed in a major groove of the third and fourth strands.

In other embodiments, the second and fourth strands are parallel to each other. In these embodiments, which possess "nested complementarity," a major groove of the first and second strands is placed in a minor groove of the third and fourth strands.

In certain embodiments, each nucleobase binds to no more than two other nucleobases. In some of these embodiments, the bases of the second strand specifically bond (via Watson-Crick rules) to the matching bases of the first strand and to the matching bases of the fourth strand, and the bases of the fourth strand specifically bond (via Watson-Crick rules) to the matching bases of the third strand and to the matching bases of the second strand, wherein the bases of the first and third strands bind to no more than one other base each. Thus, in addition to the traditional Watson-Crick base pairs, such embodiments include the following Watson-Crick base triplets: A-T-A, T-A-T, U-A-T, T-A-U, A-U-A, U-A-U, G-C-G and/or C-G-C (including $C^+$-G-C, and/or any other ionized species of base).

Figure 6:
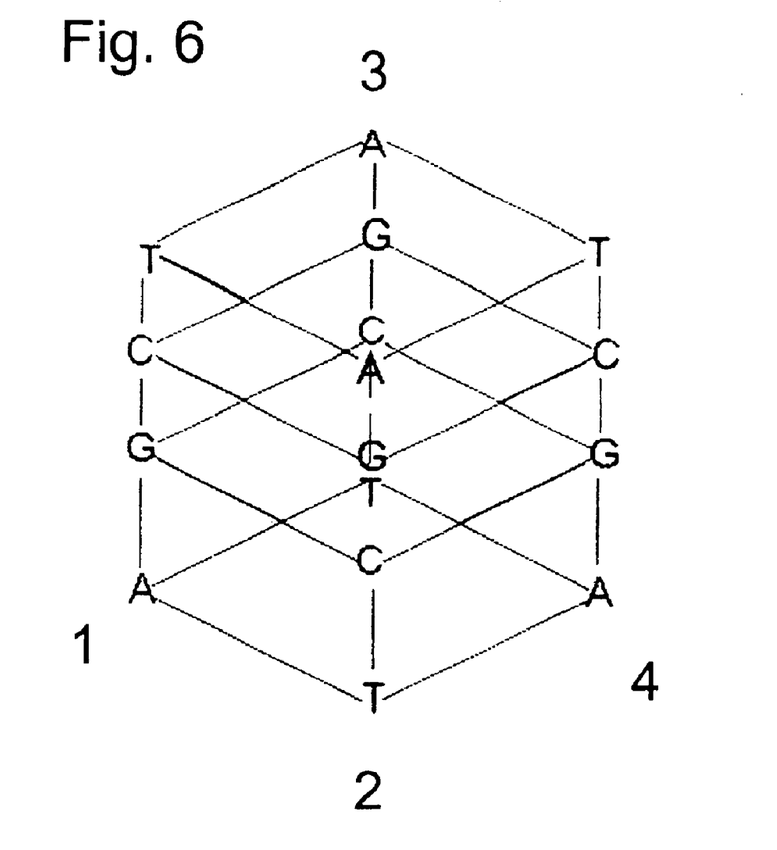
FIG. 6 is a schematic representation of a quadruplex of the invention.

In certain embodiments, it is believed that opposing bases of the first and third strands also bind to each other, in addition to: (a) the binding between opposing bases of the first and second strands; (b) the binding between opposing bases of the third and fourth strands; and (c) the binding between opposing bases of the second and fourth strands. See FIG. 6.

In certain embodiments of the multiplex structure of the invention, no strand is contiguous with another strand. That is, there are at least four separate strands. Although folded conformations and the like (e.g., hairpin turns, etc.) are within the scope of the invention, folded portions of a single strand do not make the strand count more than once toward the minimum of four separate strands.

Multiplex structures of the invention preferably do not rely on Hoogsteen bonding or G—G quartets for maintenance of the multiplex structure, although insignificant amounts of Hoogsteen bonding and/or G—G quartets may be present. That is, multiplex structures of the invention are preferably substantially free of Hoogsteen bonding, and substantially free of G—G quartets.

In certain embodiments, the first and second strands of the multiplex are 5 to 50 bases long (more preferably 5 to 30 bases long) and the third and fourth strands are 8 to $3.3 \times 10^9$ base pairs long. For example, the first and second strands can constitute a double-stranded probe and the third and fourth strands can constitute a double-stranded target, such as genomic DNA, which can contain a haplotype.

In embodiments, the third strand and the fourth strand are PCR amplified products.

The multiplexes of the invention can be present in solution, on a solid support, in vitro or in vivo. The solid support can be electrically conductive (e.g., an electrode) or non-conductive.

Quadruplex formation according to the invention is suitable for a variety of uses. For example, double-stranded probes covalently bound to a double-stranded nucleic acid cleaving agent can be used to specifically cleave target sequences of double-stranded nucleic acids. Double-stranded probes covalently bound to a chemotherapeutic agent can be used to specifically treat target sequences of double-stranded nucleic acids. Thus, the invention encompasses multiplex structures further comprising a therapeutic, prophylactic or diagnostic agent bound to at least one of the first, second, third and fourth strands.

In addition, multiplexes of the invention are suitable for use in nanoengineering, such as to provide electrical circuitry on a molecular (i.e., nanoscale) level. Further details regarding nanoengineering with nucleic acids can be found in U.S. Pat. No. 5,948,897 to Sen et al. and the references cited therein.

Multiplex structures of the invention can be provided by a method comprising: providing a hybridization medium comprising the first strand, the second strand, the third strand, the fourth strand, water, a buffer and a promoter; and incubating the hybridization medium for an incubation time effective to hybridize the second strand to the fourth strand.

The hybridization medium can include any conventional medium known to be suitable for preserving nucleotides. See, e.g., Sambrook et al., "Molecular Cloning: A Lab Manual," Vol. 2 (1989). For example, the medium can comprise nucleotides, water, buffers and standard salt concentrations. When divalent cations are used exclusively to promote quadruplex formation, chelators such as EDTA or EGTA should not be included in the reaction mixtures.

Specific binding between complementary bases occurs under a wide variety of conditions having variations in temperature, salt concentration, electrostatic strength, and buffer composition. Examples of these conditions and methods for applying them are known in the art.

Unlike many Hoogsteen-type multiplexes, which are unstable or non-existent at pH levels above about 7.6, the Watson-Crick multiplexes of the invention are stable over a wide range of pH levels, preferably from about pH 5 to about pH 9.

Moreover, the inventive multiplexes do not require the presence of homopyrimidine sequences or homopurine sequences, as in certain prior art quadruplexes. For example, the target sequence can contain 25% to 75% purine bases and 75% to 25% pyrimidine bases in any order.

It is preferred that multiplexes be formed at a temperature of about 5° C. to about 25° C. for about two hours or less. The incubation time is preferably less than five minutes, even at room temperature. Longer reaction times are not required, but incubation for up to 24 hours in most cases did not adversely affect the quadruplexes. The fast binding times of Watson-Crick quadruplexes of the invention contrast with the much longer binding times for Hoogsteen quadruplexes.

The promoter in the hybridization medium is preferably an intercalating agent or a cation. The intercalating agent can be, e.g., a fluorophore, such as a member selected from the group consisting of YOYO-1, TOTO-1, ethidium bromide, ethidium homodimer-1, ethidium homodimer-2 and acridine.

Suitable cations include, e.g., monovalent cations, such as $Na^+$ (preferably at a concentration of 50 mM to 125 mM), $K^+$, and other alkali metal ions; divalent cations, such as alkaline earth metal ions (e.g., $Mg^{+2}$ and $Ca^{+2}$) and divalent transition metal ions (e.g., $Mn^{+2}$, $Ni^{+2}$, $Cd^{+2}$, $Co^{+2}$ and $Zn^{+2}$); and cations having a positive charge of at least three, such as $Co(NH_3)_6^{+3}$, trivalent spermidine and tetravalent spermine. $Mn^{+2}$ is preferably provided at a concentration of 10 mM to 30 mM. $Mg^{+2}$ is preferably provided at a concentration of 15 mM to 20 mM. $Ni^{+2}$ is preferably provided at a concentration of about 20 mM. In embodiments, $Mg^{+2}$ and $Mn^{+2}$ are provided in combination at a concentration of 10 mM each, 15 mM each, 20 mM each, 25 mM each or 30 mM each (i.e., 10–30 mM each).

The amount of cation added to the medium in which the multiplex forms depends on a number of factors, including the nature of the cation, the concentration of probe, the concentration of target, the presence of additional cations and the base content of the probe and target. The preferred cation concentrations and mixtures can routinely be discovered experimentally.

Although not required, other promoters include, e.g., single stranded binding proteins such as Rec A protein, T4 gene 32 protein, *E. coli* single stranded binding protein, major or minor nucleic acid groove binding proteins, viologen and additional intercalating substances such as actinomycin D, psoralen, and angelicin. Such facilitating reagents may prove useful in extreme operating conditions, for example, under abnormal pH levels or extremely high temperatures.

The invention also enables a method in which hybridization of the second strand to the fourth strand inactivates an activity associated with at least one of the third strand and the fourth strand. Thus, at least one of the first strand and the second strand further comprises a pharmaceutical agent, wherein hybridization of the second strand to the fourth strand places the pharmaceutical agent an effective distance from a target on the third strand, the fourth strand or on another molecule associated with at least one of the third strand and the fourth strand. The pharmaceutical agent is preferably a member selected from the group consisting of nucleic acids designed to bind promoter sequences of clinically relevant genes, nucleic acids designed to bind clinically relevant genes, or nucleic acids designed to bind origin of replication sites of pathogens.

In preferred embodiments, the invention provides a rapid, sensitive, environmentally friendly, and safe method for assaying binding between a single-stranded or double-stranded target and a double-stranded probe, wherein the target comprises a nucleic acid sequence or a nucleic acid analogue sequence and the probe comprises a nucleic acid sequence or a nucleic acid analogue sequence.

The inventive assay can be used to, e.g., identify accessible regions in folded nucleotide sequences, to determine the number of mismatched base pairs in a hybridization complex, and to map genomes.

The invention not only detects the presence of specific probe-target binding, but also provides qualitative and quantitative information regarding the nature of interaction between a probe and target. Thus, the invention enables the practitioner to distinguish among a perfect match, a one base pair mismatch, a two base pair mismatch, a three base pair mismatch, a one base pair deletion, a two base pair deletion and a three base pair deletion arising between a sequence in the double-stranded probe and in a sequence in the double-stranded target.

Embodiments of the invention comprise calibrating the measured signal (e.g., fluorescence, chemiluminescence, electrochemiluminescence or electrical properties) for a first probe-target mixture against the same type of signal exhibited by other probes combined with the same target, wherein each of the other probes differs from the first probe by at least one base.

A calibration curve can be generated, wherein the magnitude of the measured signal (e.g., fluorescent intensity) is a function of the binding affinity between the target and probe. As the binding affinity between the target and a plurality of different probes varies with the number of mismatched bases, the nature of the mismatch(es) (A-G vs. A-C vs. T-G vs. T-C, etc.), the location of the mismatch(es) within the quadruplex, etc., the assay of the invention can be used to sequence the target.

In embodiments, the signal measured can be the fluorescent intensity of a fluorophore included in the test sample. In such embodiments, the binding affinity between the probe and target can be directly or inversely correlated with the intensity, depending on whether the fluorophore signals hybridization through signal quenching or signal amplification. Under selected conditions, the fluorescent intensity generated by intercalating agents can be directly correlated with probe-target binding affinity, whereas the intensity of preferred embodiments employing a non-intercalating fluorophore covalently bound to the probe can be inversely correlated with probe-target binding affinity. The fluorescent intensity decreases for non-intercalating fluorophores as the extent of matching between the probe and target increases, preferably over a range inclusive of 0–2 mismatches and/or deletions, more preferably over a range inclusive of 0–3 mismatches and/or deletions.

The invention enables quantifying the binding affinity between probe and target. Such information can be valuable for a variety of uses, including designing antisense drugs with optimized binding characteristics.

The assay of the invention is preferably homogeneous. The assay can be conducted without separating the probe-target complex from the free probe and free target prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated. Furthermore, it enables binding variables such as buffer, pH, ionic concentration, temperature, incubation time, relative concentrations of probe and target sequences, intercalator concentration, length of target sequences, length of probe sequences, and possible cofactor (i.e., promoter) requirements to be rapidly determined.

The assay can be conducted in, e.g., a solution within a well or microchannel, on an impermeable surface or on a biochip. In certain embodiments, the third and fourth strands are provided in the hybridization medium before the first and second strands, and the first and second strands are provided in dehydrated form prior to rehydration by contact with the hybridization medium.

Moreover, the inventive assay is preferably conducted without providing a signal quenching agent on the target or on the probe.

Although the inventors have previously disclosed the advantages of fluorescent intensity assays for hybridization (see, e.g., U.S. patent application Ser. No. 09/224,505, filed Dec. 31, 1998), certain embodiments of the inventive assay specifically detect quadruplexes of the probe and the double-stranded target, thus obviating the need to denature the target. It is surprising that the inventors have been able to specifically assay quadruplexes formed between double-stranded probes and double-stranded targets, wherein the interaction between the probes and targets is based on Watson-Crick base pairing (at least in the sense that A binds to T (or U, in the case of RNA) and G binds to C), rather than the very limited Hoogsteen model of quadruplex hybridization of, e.g., Pitner et al., supra.

Suitable probes for use in the inventive assay include, e.g., dsDNA, dsRNA, DNA:RNA hybrids, dsPNA, PNA:DNA hybrids and other double-stranded nucleic acid analogues having uncharged or partially-charged backbones. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. In embodiments, probes of 5 to 30 bases are most preferred. However, a plurality of shorter probes can be used to detect a nucleotide sequence having a plurality of non-unique target sequences therein, which combine to uniquely identify the nucleotide sequence. The length of the probe can be selected to match the length of the target.

The instant invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

In embodiments, the probe is labeled with a multi-molecule signaling complex or a redox pair, or with a label that elicits chemiluminescent or electrochemiluminescent properties.

When a fluorescent intercalator is not present in the hybridization medium, it is preferred that the probe or target (preferably the probe) have a fluorescent label covalently bound thereto. The label is preferably a non-intercalating fluorophore or an intercalating fluorophore. In such embodiments, the fluorophore is preferably bound to the probe at either end. Preferred fluorescent markers include biotin, rhodamine, acridine and fluorescein, and other markers that fluoresce when irradiated with exciting energy.

The excitation wavelength is selected (by routine experimentation and/or conventional knowledge) to correspond to this excitation maximum for the fluorophore being used, and is preferably 200 to 1000 nm. Fluorophores are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from 5 to 85° C. Certain prior art assays require elevated temperatures, adding cost and delay to the assay. On the other hand, the invention can be conducted at room temperature or below (e.g., at a temperature below 25° C.).

The reliability of the invention is independent of guanine and cytosine content in said target. Since G-C base pairs form three hydrogen bonds, while A-T base pairs form only two hydrogen bonds, target and probe sequences with a higher G or C content are more stable, possessing higher melting temperatures. Consequently, base pair mismatches that increase the GC content of the hybridized probe and target region above that present in perfectly matched hybrids may offset the binding weakness associated with a mismatched probe.

The inventive assay is extremely sensitive, thereby obviating the need to conduct PCR amplification of the target. For example, it is possible to assay a test sample having a volume of about 20 microliters, which contains about 10 femtomoles of target and about 10 femtomoles of probe. Embodiments of the invention are sensitive enough to assay targets at a concentration of $5 \times 10^{-9}$ M, preferably at a concentration of not more than $5 \times 10^{-10}$ M. Embodiments of the invention are sensitive enough to employ probes at a concentration of $5 \times 10^{-9}$ M, preferably at a concentration of not more than $5 \times 10^{-10}$ M. It should go without saying that the foregoing values are not intended to suggest that the method cannot detect higher concentrations.

The ratio of probe (e.g., first and second strands) to target (e.g., third and fourth strands) is 30:1 to 1:1, preferably about 10:1.

The invention will be illustrated in more detail with reference to the following Examples, but it should be understood that the present invention is not deemed to be limited thereto.

EXAMPLES

Example 1

Sense and antisense 50-mer ssDNA target sequences, derived from exon 10 of the human cystic fibrosis gene (Nature 380, 207 (1996)) and modified such that the percent GC content was changed from 30% to 52%, were synthesized on a DNA synthesizer (Expedite 8909, PerSeptive Biosystems) and purified by HPLC. Equimolar amounts of complementary oligonucleotides were denatured at 95° C. for 10 minutes and allowed to anneal gradually as the temperature cooled to 21° C. over 1.5 hours. DsDNA oligonucleotides were dissolved in ddH$_2$O at a concentration of 1 pmole/µl.

Sequence for the sense strand (SEQ ID NO:1) of the wild-type dsDNA Target A: 5'-GAG CAC CAT GAC AGA CAC TGT CAT CTC TGG TGT GTC CTA CGA TGA CTC TG-3'.

Sequence for the antisense strand (SEQ ID NO:2) of the wild-type dsDNA Target A: 5'-CAG AGT CAT CGT AGG ACA CAC CAG AGA TGA CAG TGT CTG TCA TGG TGC TC-3'.

Target B was a 50-mer mutant dsDNA target identical to the wild-type target DNA except for a one base pair mutation (underlined) on the sense and antisense strands, wherein the wild-type bases CAT and ATG were replaced by bases C<u>G</u>T and A<u>C</u>G, respectively.

Sequence for the sense strand (SEQ ID NO:3) of mutant Target B: 5'-GAG CAC CAT GAC AGA CAC TGT C<u>G</u>T CTC TGG TGT GTC CTA CGA TGA CTC TG-3'.

Sequence for the antisense strand (SEQ ID NO:4) of mutant Target B: 5'-CAG AGT CAT CGT AGG ACA CAC CAG AGA <u>C</u>GA CAG TGT CTG TCA TGG TGC TC-3'.

Target C was a 50-mer mutant dsDNA target identical to the wild-type target DNA except for a one base pair mutation (underlined) on the sense and antisense strands, wherein the wild-type bases CAT and ATG were replaced by bases C<u>T</u>T and A<u>A</u>G, respectively.

Sequence for the sense strand (SEQ ID NO:5) of mutant Target C: 5'-GAG CAC CAT GAC AGA CAC TGT C<u>T</u>T CTC TGG TGT GTC CTA CGA TGA CTC TG-3'.

Sequence for the antisense strand (SEQ ID NO:6) of mutant Target C: 5'-CAG AGT CAT CGT AGG ACA CAC CAG AGA <u>A</u>GA CAG TGT CTG TCA TGG TGC TC-3'.

Target D was a 50-mer mutant dsDNA target identical to the wild-type DNA except for a one base pair mutation (underlined) on the sense and antisense strands, wherein the wild-type bases CTC and GAG were replaced by bases CT <u>T</u> and <u>A</u>AG, respectively.

Sequence for the sense strand (SEQ ID NO:7) of mutant Target D: 5'-GAG CAC CAT GAC AGA CAC TGT CAT CT <u>T</u> TGG TGT GTC CTA CGA TGA CTC TG-3'.

Sequence for the antisense strand (SEQ ID NO:8) of mutant Target D: 5'-CAG AGT CAT CGT AGG ACA CAC CA<u>A</u> AGA TGA CAG TGT CTG TCA TGG TGC TC-3'.

Target E was a 50-mer mutant dsDNA target identical to the wild-type DNA except for a one base pair mutation (underlined) on the sense and antisense strands, wherein the wild-type bases CTC and GAG were replaced by bases C<u>C</u>C and G<u>G</u>G, respectively.

Sequence for the sense strand (SEQ ID NO:9) of mutant Target E: 5'-GAG CAC CAT GAC AGA CAC TGT CAT C <u>C</u>C TGG TGT GTC CTA CGA TGA CTC TG-3'.

Sequence for the antisense strand (SEQ ID NO:10) of mutant Target E: 5'-CAG AGT CAT CGT AGG ACA CAC CAG <u>G</u>GA TGA CAG TGT CTG TCA TGG TGC TC-3'.

Probe A was a 15-mer dsDNA probe with an attached fluorescein moiety at each 5' position and was designed to be mirror complementary to 15 nucleotide segments of the sense strand and antisense strand near the center of the 50-mer wild-type Target A. The strands of the probe were synthesized on the DNA synthesizer mentioned above and purified by HPLC. Equimolar amounts of the probe strands were denatured at 95° C. for 10 min and allowed to anneal as the temperature cooled to 21° C. over 1.5 hours. DsDNA probe was dissolved in ddH$_2$O at a concentration of 1 pmole/µl.

Sequence for the sense strand (SEQ ID NO:11) of Probe A: 5'-Flu-CTG TCA TCT CTG GTG-3'.

Sequence for the antisense strand (SEQ ID NO:12) of Probe A: 5'-Flu-CAC CAG AGA TGA CAG-3'.

Figure 1:
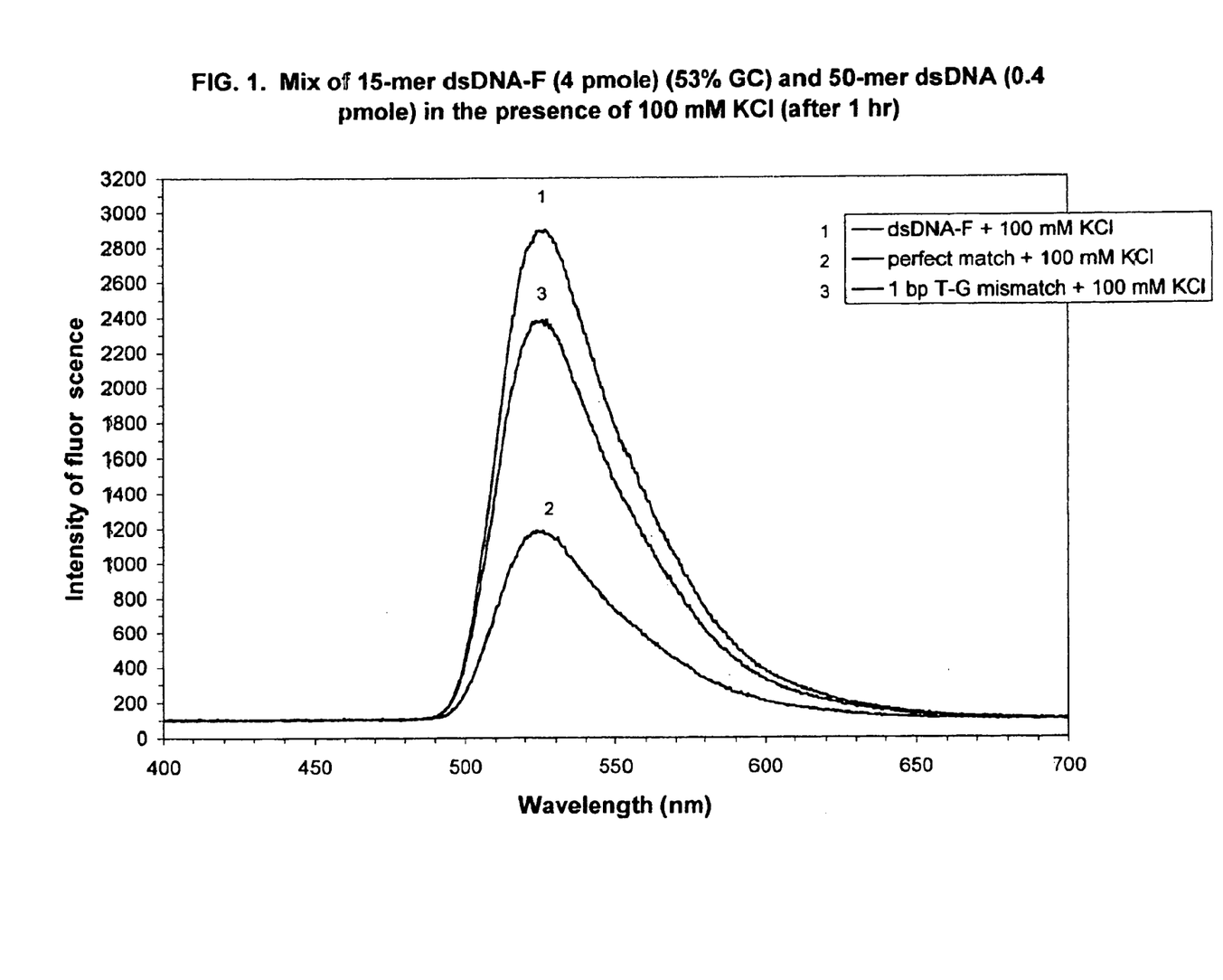
FIGS. 1, 2, 3, 4 and 5 are composite graphs of fluorescent intensity plotted as a function of wavelength for each sample analyzed.

Each hybridization reaction mixture (40 µl) contained the following: 0.4 pmoles of target dsDNA, 4 pmoles of 5'-fluorescein labeled dsDNA probe, 10 mM Tris-HCl, pH 7.5 and 100 mM KCl. The reaction mixtures were incubated at room temperature (21° C.) for 1 hour, without prior denaturation. Samples were placed into a quartz cuvette, irradiated with an argon ion laser beam having a wavelength of 488 nm and monitored for fluorescent emission. The maximum fluorescent intensities occurred at a wavelength of 525 nm, the emission wavelength for fluorescein. FIG. 1 shows the intensity of fluorescence plotted as a function of wavelength for each sample analyzed.

In the absence of KCl, no hybridization between the dsDNA targets and the Probe A was detected, resulting in similar fluorescent intensities observed when wild-type dsDNA Target A or mutant dsDNA Target D were mixed with dsDNA Probe A or when dsDNA Probe A was present alone (data not shown).

After a 1 hour incubation at 21° C. in the presence of 100 mM KCl, dsDNA target:dsDNA-F quadruplexes consisting of perfectly complementary sequences on dsDNA Target A and dsDNA Probe A formed readily, resulting in a 62% decrease in the intensity of fluorescent emission compared to that emitted by dsDNA Probe A alone (labeled dsDNA-F) (FIG. 1). In contrast, incompletely complementary dsDNA Target D:dsDNA-F Probe A quadruplexes, containing a 1 base pair G-T mismatch, were less stable in these reaction conditions, yielding only an 18% decrease in fluorescent intensity compared to that exhibited by dsDNA Probe A alone.

The presence of monovalent cations, such as K$^+$, at specific concentrations was sufficient to allow quadruplex formation between dsDNA targets and dsDNA probes labeled with fluorescein in the absence of prior denaturation. Quadruplex formation occurred on the basis of Watson-Crick base pair affinities, with a measurable and significantly greater amount of quadruplex formation between fully complementary homologous duplex strands. Moreover, the reaction occurred at room temperature within just 1 hour of incubation at a ratio of probe to target of 10 to 1, using natural dsDNA. The dsDNA targets and dsDNA probe used in this example were homologous, contained 53% GC content, and did not contain homopurine or homopyrimidine stretches on any DNA strand. DNA quadruplexes formed readily despite the inferred conclusion that the formation required the duplex probe to give up its right-handed chirality. The assay of the invention was able to identify perfectly complementary dsDNA sequences and those containing a pair of mismatched bases, using dsDNA probe.

Example 2

The quadruplex DNA assays performed in Example 1 were facilitated by the addition of monovalent cations to the reaction mixtures. The specificity of the assay was further examined utilizing divalent cations to facilitate quadruplex DNA formation with dsDNA targets and dsDNA-F probes possessing 53% GC content.

Figure 2:
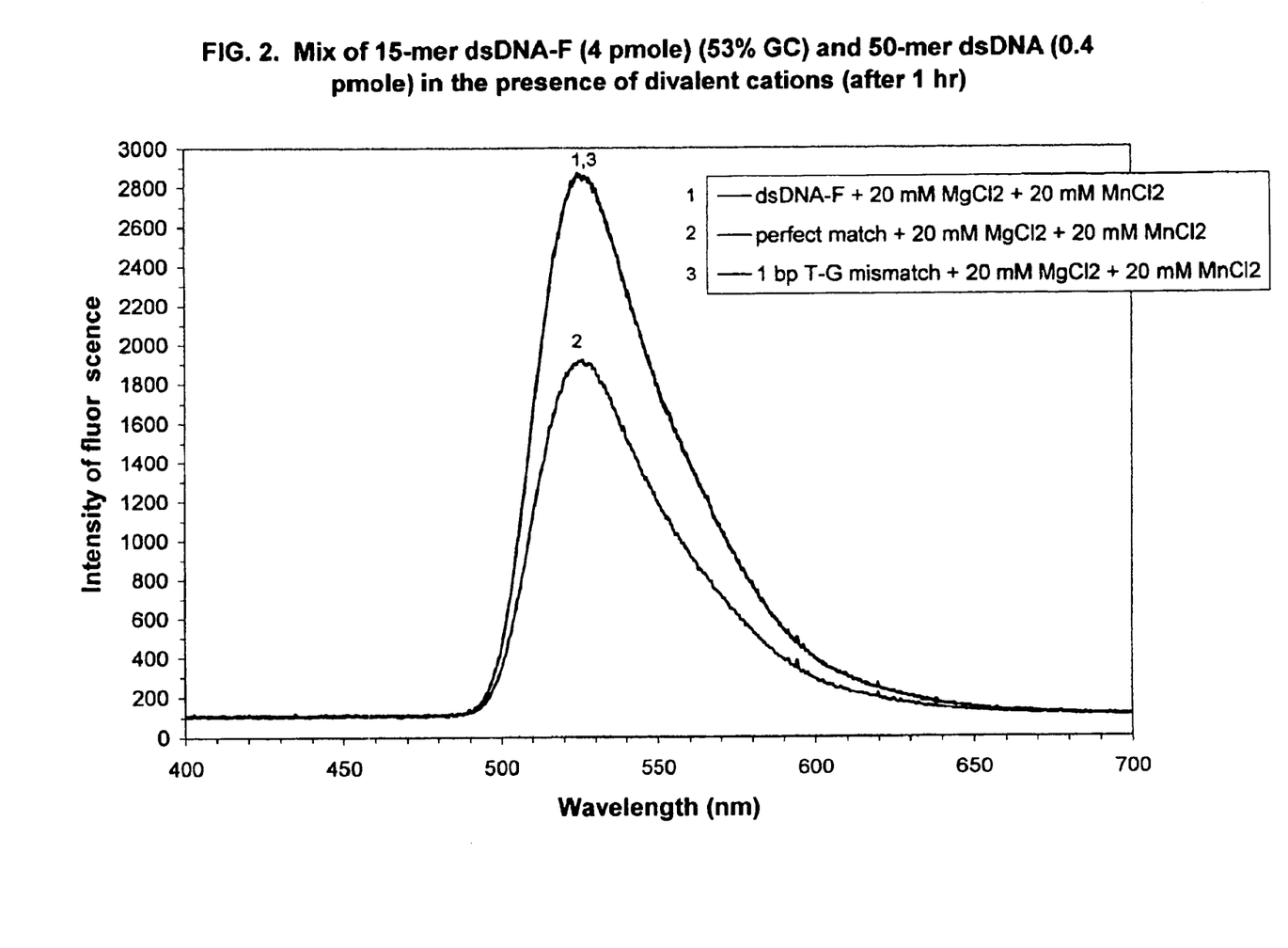

Each hybridization reaction mixture (40 µl) contained the following: 0.4 pmoles of target dsDNA, 4 pmoles of 5'-fluorescein labeled dsDNA probe, 10 mM Tris-HCl, pH 7.5 and 20 mM MnCl$_2$ and 20 mM MgCl$_2$. The reaction mixtures were incubated at room temperature (21° C.) for 1 hour, without prior denaturation. Samples were placed into a quartz cuvette, irradiated with an argon ion laser beam having a wavelength of 488 nm and monitored for fluorescent emission. FIG. 2 shows the intensity of fluorescence plotted as a function of wavelength for each sample analyzed.

When dsDNA-F Probe A (with a 53% GC content) was incubated with 50-mer wild-type dsDNA Target A or mutant dsDNA Target D in the presence of 20 mM MnCl$_2$ and 20 mM MgCl$_2$, quadruplexes were formed at room temperature under non-denaturing conditions. While perfectly matched DNA quadruplexes yielded the maximum decrease in fluorescent intensity, a 34% decrease, the less favorable dsDNA:dsDNA-F quadruplexes containing a 1 bp T-G mismatch (dsDNA Target D+dsDNA Probe A) produced a fluorescent intensity that was about the same as that observed with dsDNA Probe A alone (FIG. 2).

The presence of divalent cations, such as Mn$^{+2}$ and Mg$^{+2}$, facilitated quadruplex formation under non-denaturing conditions to allow accurate discrimination between homologous, that is mirror complementary, dsDNA target and dsDNA probe quadruplexes, and quadruplex sequences containing a pair of bases which are mismatched.

Divalent cations facilitated the formation of mirror complementary Watson-Crick quadruplexes despite the inferred conclusion that the formation required the duplex probe to give up its right-handed chirality.

Example 3

The quadruplex DNA assays performed in Examples 1 and 2 were facilitated by the addition of either monovalent cations or divalent cations in the reaction mixtures. The next Examples demonstrate the specificity of the quadruplex DNA assays when a DNA intercalator is employed.

Probe B was a 15-mer dsDNA probe identical to probe A, without the attached fluorescein marker, and was prepared similarly.

Each hybridization reaction mixture (40 µl) contained the following: 0.4 pmoles of dsDNA target, 4 pmoles of dsDNA Probe B, 0.5×TBE and 100 nM of the DNA intercalator YOYO-1 (Molecular Probes, Eugene, Oreg., USA). The reaction mixtures were incubated at 21° C. for 5 minutes and then assayed. Samples were placed into a quartz cuvette, and irradiated with an argon ion laser beam having a wavelength of 488 nm. The maximum fluorescent intensity occurred at a wavelength of 535 nm, indicative of intercalation of YOYO-1.

Figure 3:
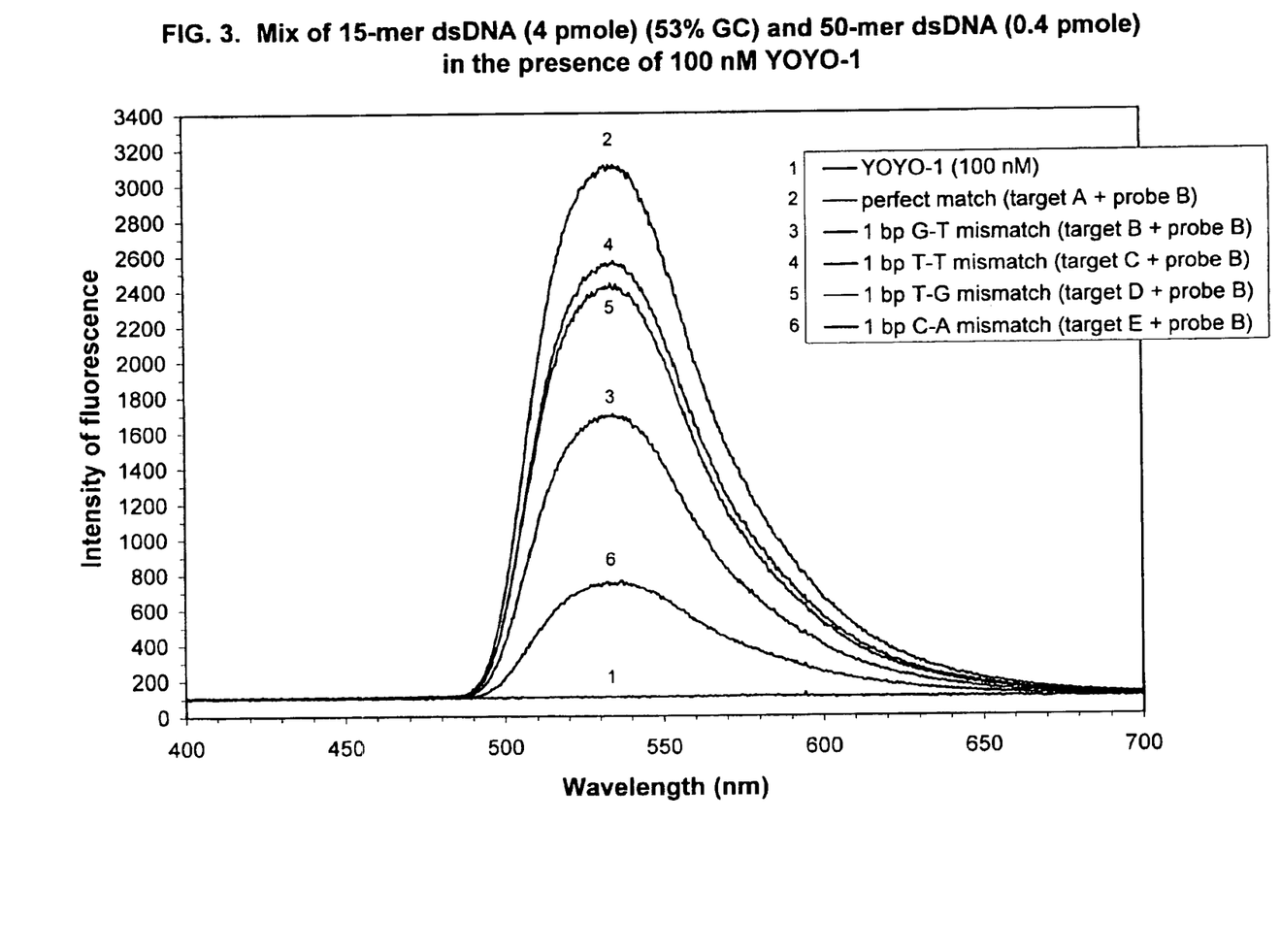

The fluorescent intensities observed when no target or probe was present (YOYO-1 only) are shown in FIG. 3. FIG. 3 also shows the fluorescent intensities observed when the reaction mixtures combined dsDNA Probe B with wild-type 50-mer dsDNA Target A, which contained homologous sequences, or with four other dsDNA targets which, but for one mismatched pair of bases, contained sequences which were homologous to the base sequences in the dsDNA Probe B. Homologous, that is to say mirror complementary, wild-type target dsDNA when present in the reaction mixture with the dsDNA Probe B produced the greatest fluorescent intensity. Mismatched dsDNA targets when incubated with dsDNA Probe B in the reaction mixture yielded lesser fluorescent intensity values ranging from 20% less for dsDNA Target C to 80% less for dsDNA Target E, compared to that achieved by perfectly matched quadruplexes (FIG. 3).

It was observed that Watson-Crick quadruplexes, stabilized by YOYO-1 intercalation, formed more readily between dsDNA target and dsDNA probe when that probe contained perfectly homologous, that is to say mirror complementary sequences, than when there was a single pair of bases which were not homologous, that is to say not mirror complementary to sequences in the dsDNA targets. Watson-Crick quadruplexes formed readily despite the inferred conclusion that the quadruplex formation required the duplex probe to give up its right-handed chirality.

Example 4

In this example, 50-mer dsDNA targets were exposed to the 53% GC 15-mer dsDNA Probe C, whose Watson-Crick complementarity exists between bases of the strands of the probe and bases of the strands of the target when the major groove of the duplex probe is placed in the minor groove of the duplex target, herein referred to as nested complementarity. The sequences of bases in the duplex probe are not homologous but inverted in relation to those in the duplex target.

The strands of the probe were synthesized on the DNA synthesizer mentioned above and purified by HPLC. Equimolar amounts of the probe strands were denatured at 95° C. for 10 min and allowed to anneal as the temperature cooled to 21° C. over 1.5 hours. DsDNA probe was dissolved in ddH$_2$O at a concentration of 1 pmole/µl.

Sequence for the sense strand (SEQ ID NO:13) of dsDNA Probe C: 5'-GAC AGT AGA GAC CAC-3'.

Sequence for the antisense strand (SEQ ID NO:14) of dsDNA Probe C: 5'-GTG GTC TCT ACT GTC-3'.

Each hybridization reaction mixture (40 µl) contained the following: 0.4 pmoles of target dsDNA, 4 pmoles of dsDNA Probe C, 0.5×TBE and 100 nM of the DNA intercalator YOYO-1. The reaction mixtures were incubated at room temperature (21° C.) for 5 minutes, placed in a quartz cuvette, and irradiated with an argon ion laser beam having a wavelength of 488 nm. The maximum fluorescent intensity occurred at a wavelength of 535 nm, indicative of intercalation of YOYO-1.

Figure 4:
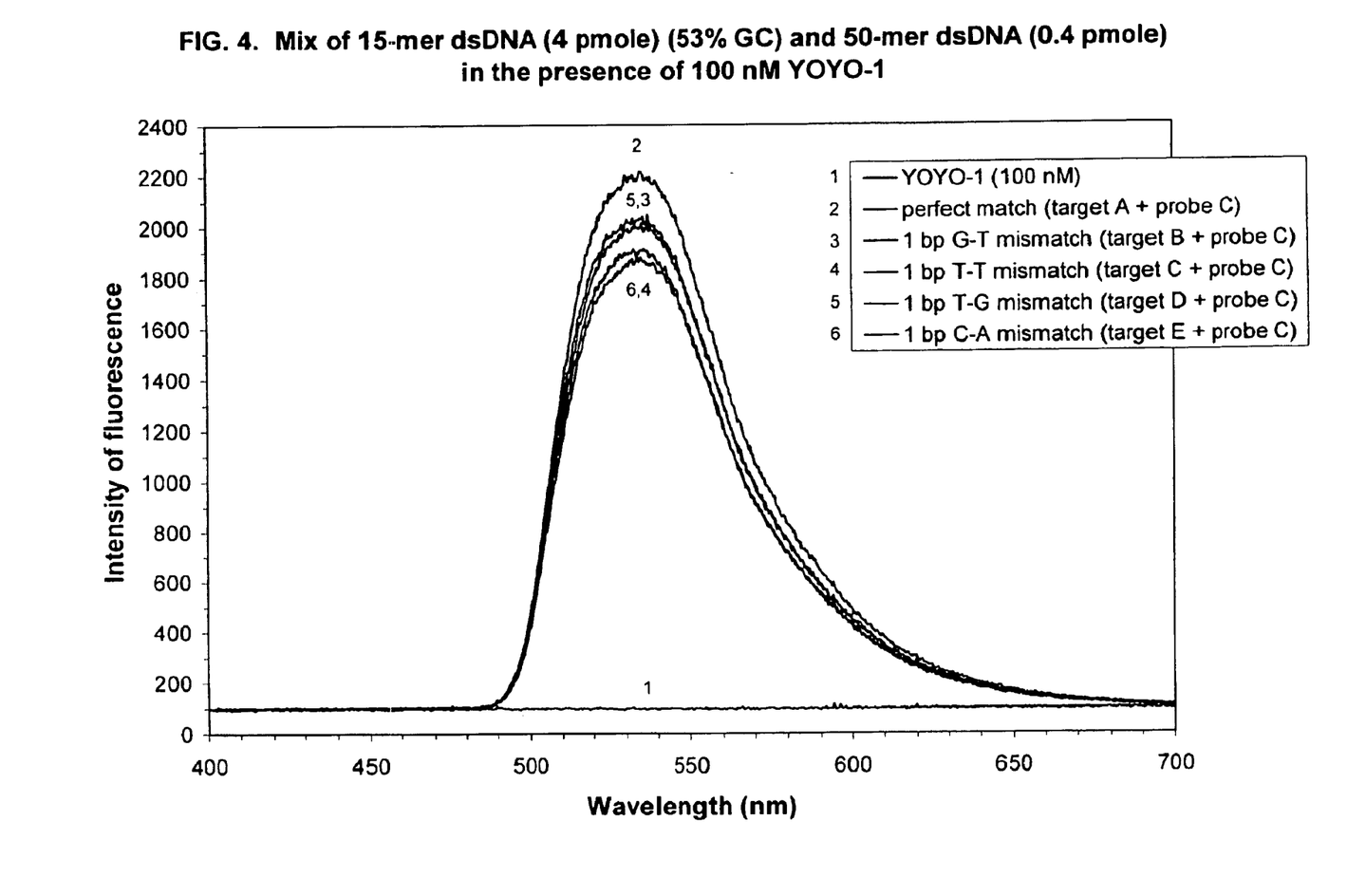

FIG. 4 illustrates that in the absence of prior denaturation, the highest fluorescent intensities were achieved when wild-type 50-mer dsDNA Target A was reacted with 15-mer dsDNA Probe C, which was a perfect match on a nested complementary basis to dsDNA Target A. The fluorescent intensity is indicative of DNA binding taking place, in this case quadruplex formation between the dsDNA target and nested complementary dsDNA probe.

Mutant dsDNA targets which were mismatched with the duplex probe by a single pair of bases when matching was assessed on the inverted homology basis of nested complementarity, formed measurably fewer quadruplex complexes with the dsDNA probe, than did the fully complementary wild-type dsDNA target. The various mismatches, which were assayed on a mirror complementary basis in Example 3 were assayed on a nested complementary basis in this example.

As shown in FIG. 4, the fluorescent intensities produced by the quadruplexes formed with the 1 bp mismatched dsDNA targets plus dsDNA Probe C, ranged from 8% to 16% less than that achieved by perfectly matched quadruplexes (dsDNA Target A+dsDNA Probe C).

Greater discrimination in fluorescence was observed between perfectly matched and mismatched quadruplexes in Example 3. This suggests that fully complementary or 1 base pair mismatched dsDNA probes prefer binding in a nested complementary orientation rather than a mirror complementary orientation to dsDNA target.

This example shows that Watson-Crick quadruplex binding between nested complementary duplex DNA readily occurs in the presence of YOYO-1. This facility arises in part from the fact that nested complementary quadruplex binding allows the right-handed chirality of each interacting duplex to be maintained.

Example 5

50-mer ssDNA target sequences, derived from exon 10 of the human cystic fibrosis gene (Nature 380, 207 (1996)) and modified such that the percent GC content was changed from 30% to 52%, were synthesized on a DNA synthesizer (Expedite 8909, PerSeptive Biosystems) and purified by HPLC.

Sequence for the strand (SEQ ID NO:2) being the 50-mer wild-type ssDNA Target F: 5'-CAG AGT CAT CGT AGG ACA CAC CAG AGA TGA CAG TGT CTG TCA TGG TGC TC-3'.

Target G was a 50-mer mutant ssDNA target identical to wild-type ssDNA Target F except for a one base mutation (underlined).

Sequence for the strand (SEQ ID NO:4) of mutant ssDNA Target G: 5'-CAG AGT CAT CGT AGG ACA CAC CAG AGA <u>C</u>GA CAG TGT CTG TCA TGG TGC TC-3'.

Target H was a 50-mer mutant ssDNA target identical to wild-type ssDNA Target F except for a one base mutation (underlined).

Sequence for the strand (SEQ ID NO:6) of mutant ssDNA Target H: 5'-CAG AGT CAT CGT AGG ACA CAC CAG AGA <u>A</u>GA CAG TGT CTG TCA TGG TGC TC-3'.

Target I was a 50-mer mutant ssDNA target identical to wild-type ssDNA Target F except for a one base mutation (underlined).

Sequence for the strand (SEQ ID NO:8) of mutant ssDNA Target I: 5'-CAG AGT CAT CGT AGG ACA CAC CA<u>A</u> AGA TGA CAG TGT CTG TCA TGG TGC TC-3'.

Target J was a 50-mer mutant ssDNA target identical to wild-type ssDNA Target F except for a one base mutation (underlined).

Sequence for the strand (SEQ ID NO:10) of mutant ssDNA Target J: 5'-CAG AGT CAT CGT AGG ACA CAC CAG <u>G</u>GA TGA CAG TGT CTG TCA TGG TGC TC-3'.

Target K was a 50-mer mutant ssDNA target identical to wild-type ssDNA Target F except for a one base mutation (underlined).

Sequence for the strand (SEQ ID NO:15) of mutant ssDNA Target K: 5'-CAG AGT CAT CGT AGG ACA CAC CAG <u>C</u>GA TGA CAG TGT CTG TCA TGG TGC TC-3'.

Probe B was a 15-mer dsDNA probe identical to Probe A without the fluorescein marker, and was prepared accordingly. One of the strands of Probe B (i.e., (SEQ ID NO:11) was complementary to a 15 nucleotide segment near the center of 50-mer wild-type ssDNA Target F.

Figure 5:
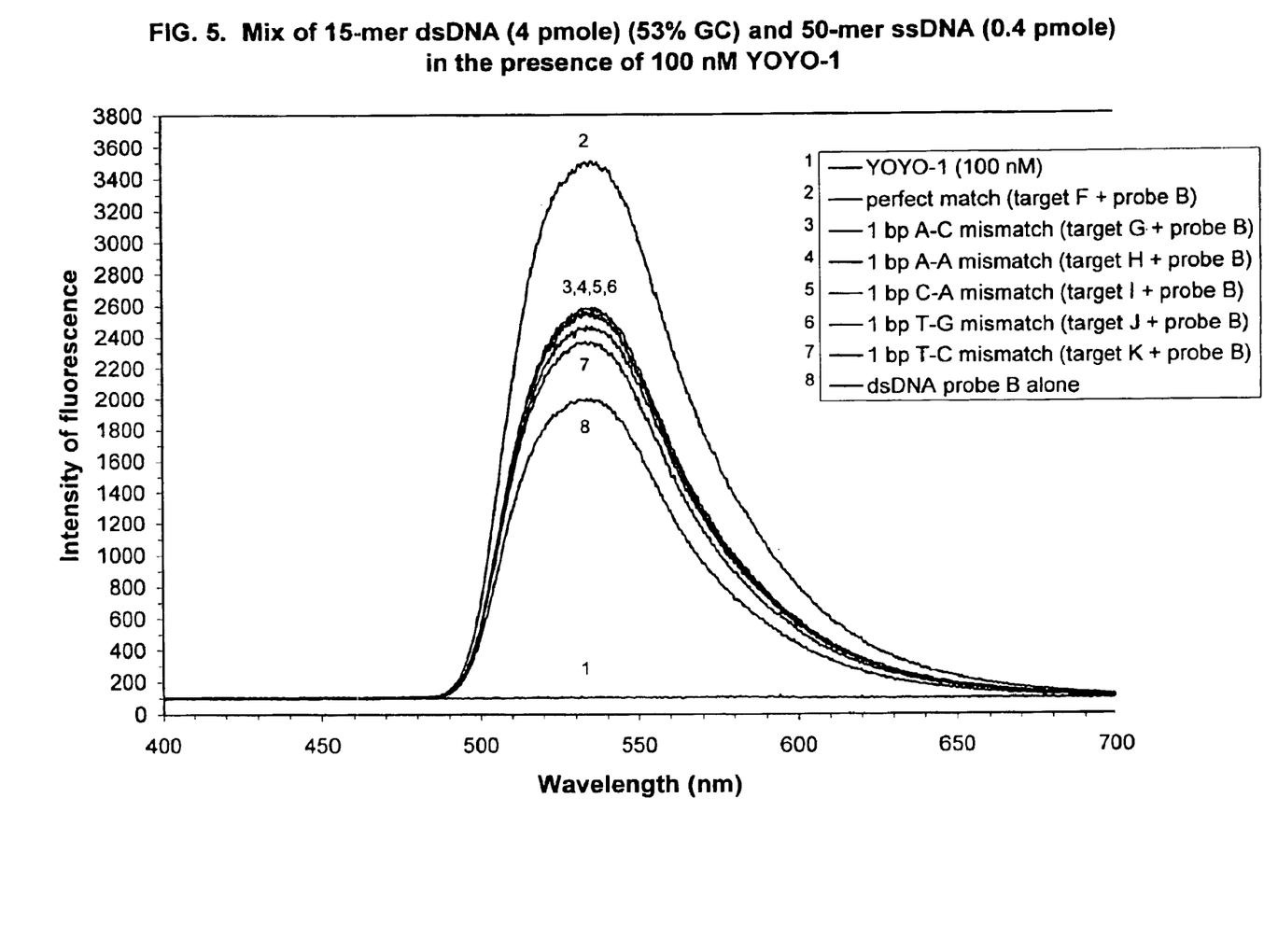

Each hybridization reaction mixture (40 μl) contained the following: 0.4 pmoles of target ssDNA, 4 pmoles of dsDNA probe, 0.5×TBE and 100 nM YOYO-1. The reaction mixtures were incubated at room temperature (21° C.) for 5 minutes, without prior denaturation. Samples were placed into a quartz cuvette, irradiated with an argon ion laser beam having a wavelength of 488 nm and monitored for fluorescent emission. Integration time of all laser irradiation was 80 msec. The maximum fluorescent intensities occurred at a wavelength of 535 nm, indicative of intercalation of YOYO-1. FIG. 5 shows the intensity of fluorescence plotted as a function of wavelength for each sample analyzed.

In the absence of target ssDNA, some hybridization between the dsDNA probes occurred on a mirror complementary basis (FIG. 5). Such binding between homologous duplex DNA is disclosed in prior examples. SsDNA targets incubated alone with YOYO-1 resulted in low intensity emission values, which were less than one-half the value of the intensity emission of the dsDNA probes alone incubated with YOYO-1 (data not shown).

After a 5 minute incubation at 21° C. in the presence of 100 mM YOYO-1, ssDNA Target F readily formed binding complexes with perfectly complementary sequences on dsDNA Probe B, resulting in a 79% increase in the intensity of fluorescent emission compared to that emitted by dsDNA Probe B alone (FIG. 5). In contrast, incompletely complementary ssDNA targets containing various one base pair mismatches were less stable in these reaction conditions, yielding only a 19% to 31% increase in fluorescent intensity compared to that exhibited by dsDNA Probe B alone (FIG. 5).

The presence of YOYO-1, an intercalator, was sufficient to allow binding between dsDNA probes and ssDNA targets in the absence of prior denaturation. Binding occurred on the basis of Watson-Crick base pair affinities, with a measurable and significantly greater amount of binding between fully complementary strands. The reaction occurred at room temperature within just 5 minutes of incubation at a ratio of probe to target of 10 to 1, using natural DNA. The ssDNA targets and dsDNA probe used in this example contained 53% GC content and did not contain homopurine or homopyrimidine stretches on any DNA strand. The assay of the invention was able to identify perfectly complementary ssDNA sequences and those containing mismatched bases, using dsDNA probes.

The assay of the invention functioned notwithstanding that binding occurred to a substantial extent between duplex probes which were fully self-complementary, i.e., of homologous strand sequence and which bound to one another in a mirror complementary fashion, that is to say major groove to major groove.

While the invention has been described in detail and with reference to specific examples thereof, it will be apparent to one skilled in the art that various changes and modifications can be made therein without departing from the spirit and scope thereof.

What is claimed is:

1. A multiplex structure comprising:
   a first strand containing a first sequence of nucleobases;
   a second strand containing a second sequence of nucleobases, wherein said second strand is associated with said first strand by Watson-Crick bonding;
   a third strand containing a third sequence of nucleobases; and
   a fourth strand containing a fourth sequence of nucleobases, wherein: (a) said fourth strand is associated with said second strand and said third strand by Watson-Crick bonding, (b) at least one nucleobase of said fourth sequence of nucleobases is associated by Watson-Crick bonding to at least one nucleobase of said third sequence of nucleobases and to at least one nucleobase of said second sequence of nucleobases, (c) each nucleobase in said second sequence and said fourth sequence binds to two other nucleobases, and (d) said multiplex structure is isolated, purified, artificial or synthetic.

2. The multiplex structure of claim 1, wherein each said strand independently comprises a nucleic acid or a nucleic acid analogue.

3. The multiplex structure of claim 2, wherein each said strand independently comprises DNA or RNA.

4. The multiplex structure of claim 2, wherein each said strand independently comprises a nucleic acid analogue containing an uncharged or partially charged backbone.

5. The multiplex structure of claim 1, wherein one of said second strand or said fourth strand comprises DNA and the other of said second strand or said fourth strand comprises RNA, mRNA, hnRNA, rRNA, tRNA or cDNA.

6. The multiplex structure of claim 1, wherein said second strand and said fourth strand are anti-parallel to each other.

7. The multiplex structure of claim 6, wherein a major groove of said first strand and said second strand is placed in a major groove of said third strand and said fourth strand.

8. The multiplex structure of claim 1, wherein said second strand and said fourth strand are parallel to each other.

9. The multiplex structure of claim 8, wherein a major groove of said first strand and said second strand is placed in a minor groove of said third strand and said fourth strand.

10. The multiplex structure of claim 1, wherein no strand is contiguous with another strand.

11. The multiplex structure of claim 1, wherein said multiplex structure is substantially free of Hoogsteen bonding.

12. The multiplex structure of claim 1, wherein said multiplex structure is substantially free of G—G quartets.

13. The multiplex structure of claim 1, wherein said first strand and said second strand are 5 to 50 base pairs long.

14. The multiplex structure of claim 1, wherein said third strand and said fourth strand are genomic DNA.

15. The multiplex structure of claim 1, wherein said third strand and said fourth strand include a haplotype in genomic DNA.

16. The multiplex structure of claim 1, wherein said third strand and said fourth strand are PCR amplified products.

17. The multiplex structure of claim 1, wherein said multiplex structure is free of solid support.

18. A multiplex structure comprising:
   a first strand containing a first sequence of nucleobases;
   a second strand containing a second sequence of nucleobases, wherein said second strand is associated with said first strand by Watson-Crick bonding;
   a third strand containing a third sequence of nucleobases; and
   a fourth strand containing a fourth sequence of nucleobases, wherein: (a) said fourth strand is associated with said second strand and said third strand by Watson-Crick bonding, (b) at least one nucleobase of said fourth sequence of nucleobases is associated by Watson-Crick bonding to at least one nucleobase of said third sequence of nucleobases and to at least one nucleobase of said second sequence of nucleobases, and (c) said multiplex structure is bound to a solid support.

19. The multiplex structure of claim 18, wherein said solid support is not electrically conductive.

20. The multiplex structure of claim 18, wherein said solid support is electrically conductive.

21. A multiplex structure comprising:
   a first strand containing a first sequence of nucleobases;
   a second strand containing a second sequence of nucleobases, wherein said second strand is associated with said first strand by Watson-Crick bonding;
   a third strand containing a third sequence of nucleobases;
   a fourth strand containing a fourth sequence of nucleobases, wherein said fourth strand is associated with said second strand and said third strand by Watson-Crick bonding, and wherein at least one nucleobase of said fourth sequence of nucleobases is associated by Watson-Crick bonding to at least one nucleobase of said third sequence of nucleobases and to at least one nucleobase of said second sequence of nucleobases; and
   a therapeutic, prophylactic or diagnostic agent bound to at least one of said first strand, said second strand, said third strand and said fourth strand.

22. A multiplex structure comprising:
a first strand containing a first sequence of nucleobases;
a second strand containing a second sequence of nucleobases, wherein said second strand is associated with said first strand by Watson-Crick bonding;
a third strand containing a third sequence of nucleobases; and
a fourth strand containing a fourth sequence of nucleobases, wherein: (a) said fourth strand is associated with said second strand and said third strand by Watson-Crick bonding, (b) at least one nucleobase of said fourth sequence of nucleobases is associated by Watson-Crick bonding to at least one nucleobase of said third sequence of nucleobases and to at least one nucleobase of said second sequence of nucleobases, (c) said multiplex structure is isolated, purified, artificial or synthetic, and (d) said first strand and said second strand are each 5 to 30 bases long and said third strand and said fourth strand are each 8 to $3.3 \times 10^9$ base pairs long.

23. The multiplex structure of claim 1, wherein said fourth sequence contains 25% to 75% purine bases and 75% to 25% pyrimidine bases in any order.

24. A method for providing the multiplex structure of claim 1, said method comprising:
providing a hybridization medium comprising said first strand, said second strand, said third strand, said fourth strand, water, a buffer and at least one promoter; and
incubating said hybridization medium for an incubation time effective to hybridize said second strand to said fourth strand to provide said multiplex structure.

25. The method of claim 24, wherein said hybridization medium is buffered to a pH of about 5 to about 9.

26. The method of claim 24, wherein said at least one promoter is an intercalating agent.

27. The method of claim 26, wherein said at least one promoter is an intercalating fluorophore, and a fluorescent intensity of a test medium containing said multiplex structure is directly correlated with a binding affinity of said second strand for said fourth strand.

28. The method of claim 27, wherein said intercalating fluorophore is a member selected from the group consisting of YOYO-1, TOTO-1, ethidium bromide, ethidium homodimer-1, ethidium homodimer-2 and acridine.

29. The method of claim 24, wherein said at least one promoter is tethered to at least one of said first strand, said second strand, said third strand and said fourth strand.

30. The method of claim 24, wherein said at least one promoter is a monovalent cation.

31. The method of claim 24, wherein said at least one promoter is a cation having a valency greater than one.

32. The method of claim 24, wherein said at least one promoter is at least one cation selected from the group consisting of alkali metal cations, alkaline earth metal cations, transition metal cations, $Co(NH_3)_6^{+3}$, trivalent spermidine and tetravalent spermine.

33. The method of claim 30, wherein said cation is $K^+$ or $Na^+$ provided at a concentration of 50 mM to 125 mM.

34. The method of claim 24, wherein said third strand and said fourth strand are provided in said hybridization medium before said first strand and said second strand, and wherein said first strand and said second strand are provided in dehydrated form prior to rehydration by contact with said hybridization medium.

35. The method of claim 24, wherein said incubation time is not more than about two hours.

36. The method of claim 24, wherein said incubating is conducted at room temperature.

37. The method of claim 24, wherein hybridization of said second strand to said fourth strand is detected as a change in a fluorescent, chemiluminescent, electrochemiluminescent or electrical signal.

38. The method of claim 37, wherein an intensity of said signal is correlated with a binding affinity between said second strand and said fourth strand.

39. The method of claim 38, wherein at least one of said first strand and said second strand is covalently labeled with a non-intercalating fluorophore and said intensity is inversely correlated with said binding affinity.

40. The method of claim 39, wherein said non-intercalating fluorophore is a member selected from the group consisting of biotin, rhodamine and fluorescein.

41. The method of claim 39, wherein said method is a homogeneous assay conducted without providing a signal quenching agent on said target sequence or on said probe.

42. The method of claim 24, wherein a ratio of said first strand and said second strand to said third strand and said fourth strand is about 10:1.

43. The method of claim 24, wherein concentrations of each of said first strand, said second strand, said third strand and said fourth strand are not more than $5 \times 10^{-10}$ M.

44. The method of claim 24, wherein said at least one promoter is a minor groove nucleic acid binding molecule, which binds in a non-intercalating manner and binds with an association constant of at least $10^3$ $M^{-1}$.

45. The multiplex structure of claim 1, wherein said first strand is associated with said third strand by Watson-Crick bonding.

* * * * *

SEQUENCE LISTING

<160> NUMBER OF SEQ ID NOS: 15

<210> SEQ ID NO 1
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 1
gagcaccatg acagacactg tcatctctgg tgtgtcctac gatgactctg          50

<210> SEQ ID NO 2
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 2

-continued cagagtcatc gtaggacaca ccagagatga cagtgtctgt catggtgctc          50

<210> SEQ ID NO 3
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 3
gagcaccatg acagacactg tcgtctctgg tgtgtcctac gatgactctg          50

<210> SEQ ID NO 4
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 4
cagagtcatc gtaggacaca ccagagacga cagtgtctgt catggtgctc          50

<210> SEQ ID NO 5
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 5
gagcaccatg acagacactg tcttctctgg tgtgtcctac gatgactctg          50

<210> SEQ ID NO 6
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 6
cagagtcatc gtaggacaca ccagagaaga cagtgtctgt catggtgctc          50

<210> SEQ ID NO 7
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 7
gagcaccatg acagacactg tcatctttgg tgtgtcctac gatgactctg          50

<210> SEQ ID NO 8
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 8

-continued cagagtcatc gtaggacaca ccaaagatga cagtgtctgt catggtgctc        50

<210> SEQ ID NO 9
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 9
gagcaccatg acagacactg tcatccctgg tgtgtcctac gatgactctg        50

<210> SEQ ID NO 10
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 10
cagagtcatc gtaggacaca ccagggatga cagtgtctgt catggtgctc        50

<210> SEQ ID NO 11
<211> LENGTH: 15
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 11
ctgtcatctc tggtg        15

<210> SEQ ID NO 12
<211> LENGTH: 15
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 12
caccagagat gacag        15

<210> SEQ ID NO 13
<211> LENGTH: 15
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 13
gacagtagag accac        15

<210> SEQ ID NO 14
<211> LENGTH: 15
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 14
gtggtctcta ctgtc        15

```
<210> SEQ ID NO 15
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 15
cagagtcatc gtaggacaca ccagcgatga cagtgtctgt catggtgctc                50
```